US00PP26784P2

(12) United States Plant Patent
Moen

(10) Patent No.: US PP26,784 P2
(45) Date of Patent: May 31, 2016

(54) *GERBERA* PLANT NAMED 'GARGLOW IMP'

(50) Latin Name: *Gerbera hybrida*
Varietal Denomination: Garglow Imp

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 137 days.

(21) Appl. No.: 14/120,585

(22) Filed: Jun. 6, 2014

(51) Int. Cl.
*A01H 5/02* (2006.01)

(52) U.S. Cl.
USPC ..... Plt./357

(58) Field of Classification Search
USPC ..... Plt./357
See application file for complete search history.

*Primary Examiner* — Keith Robinson
(74) *Attorney, Agent, or Firm* — C. A. Whealy

(57) ABSTRACT

A new and distinct cultivar of *Gerbera* plant named 'Garglow Imp', characterized by its relatively compact, broadly upright and uniformly mounding plant habit; dense and bushy appearance; numerous inflorescences with bright orange-colored ray florets; upright and strong scapes; and good garden performance.

1 Drawing Sheet

Botanical designation: *Gerbera hybrida.*
Cultivar denomination: 'GARGLOW IMP'.

BACKGROUND OF THE INVENTION

The present invention relates to a new and distinct cultivar of *Gerbera* plant, botanically known as *Gerbera hybrida* and hereinafter referred to by the name 'Garglow Imp'.

The new *Gerbera* plant is a product of a planned breeding program conducted by the Inventor in De Kwakel, The Netherlands. The objective of the breeding program is to create new compact *Gerbera* plants with numerous inflorescences, good garden performance, frost tolerance and attractive inflorescence coloration.

The new *Gerbera* plant is a naturally-occurring whole plant mutation of *Gerbera hybrida* 'Garglow', not patented. The new *Gerbera* plant was discovered and selected by the Inventor as a single flowering plant within a population of plants of 'Garglow' in a controlled greenhouse environment in De Kwakel, The Netherlands in November, 2012.

Asexual reproduction of the new *Gerbera* plant by cuttings and by tissue culture in a controlled environment in De Kwakel, The Netherlands since November, 2012 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garglow Imp'. These characteristics in combination distinguish 'Garglow Imp' as a new and distinct *Gerbera* plant:

1. Relatively compact, broadly upright and uniformly mounding plant habit.

2. Dense and bushy appearance.
3. Numerous inflorescences with bright orange-colored ray florets.
4. Upright and strong scapes.
5. Good garden performance.

Plants of the new *Gerbera* differ from plants of the parent, 'Garglow', in the following characteristics:

1. Plants of the new *Gerbera* are more vigorous than plants of 'Garglow'.
2. Plants of the new *Gerbera* have larger leaves than plants of 'Garglow'.
3. Plants of the new *Gerbera* have larger inflorescences than plants of 'Garglow'.

Plants of the new *Gerbera* can be compared to plants of the *Gerbera hybrida* 'Garrachel', disclosed in U.S. Plant Pat. No. 22,443. Plants of the new *Gerbera* differ from plants of 'Garrachel' in the following characteristics:

1. Plants of the new *Gerbera* have larger inflorescences with longer ray florets than plants of 'Garrachel'.
2. Plants of the new *Gerbera* and 'Garrachel' differ in ray floret color as plants of 'Garrachel' have red-colored ray florets.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garglow Imp' grown in a container.

DETAILED BOTANICAL DESCRIPTION

The aforementioned photograph and following observations and measurements describe plants grown during the autumn and winter in 15-cm containers in a glass-covered greenhouse in De Kwakel, The Netherlands and under cultural practices typical of commercial *Gerbera* production. During the production of the plants, day and night temperatures ranged from 10° C. to 16° C. Rooted tissue-cultured plants were 25 and 26 weeks old when the description and photograph, respectively, were taken. In the following description, color references are made to The Royal Horticultural Society Colour Chart, 2007 edition, except where general terms of ordinary dictionary significance are used.

Botanical classification: *Gerbera hybrida* 'Garglow Imp'.

Parentage: Naturally-occurring whole plant mutation of *Gerbera hybrida* 'Garglow', not patented.

Propagation:

*Type*.—By tissue culture.

*Time to initiate roots, summer and winter*.—About 2.5 to 3 weeks at temperatures about 20° C.

*Time to produce a rooted young plant, summer and winter*.—About five to six weeks at temperatures about 20° C. to 26° C.

*Root description*.—Fibrous.

Plant description:

*Appearance*.—Herbaceous perennials that are typically grown as container or garden plants; relatively compact and uniformly mounding plant habit, broadly upright and roughly globular in shape; numerous leaves arranged in basal rosettes and outwardly arching; dense and bushy habit; inflorescences held above the foliar plane on erect and strong basal scapes; moderately vigorous growth habit.

*Plant height, soil level to top of foliar plane*.—About 18 cm.

*Plant height, soil level to top of inflorescences*.—About 31 cm.

*Plant width*.—About 29.4 cm

Leaf description:

*Arrangement*.—Alternate, simple.

*Length*.—About 13.4 cm.

*Width*.—About 7.7 cm.

*Shape*.—Narrowly obovate; runcinate.

*Apex*.—Obtuse to broadly acute.

*Base*.—Acuminate.

*Margin*.—Coarsely and irregularly angulate; sinuses divergent; slightly undulate.

*Texture, upper surface*.—Slightly pubescent.

*Texture, lower surface*.—Densely tomentose.

*Venation pattern*.—Pinnate.

*Color*.—Developing leaves, upper surface: Darker than 141A. Developing leaves, lower surface: Close to 137B. Fully expanded leaves, upper surface: Close to N137B; venation, close to 144A. Fully expanded leaves, lower surface: Close to 147B; venation, close to 144A.

*Petioles*.—Length: About 5.5 cm. Diameter: About 3 mm. Texture, upper surface: Moderately pubescent. Texture, lower surface: Densely pubescent. Color, upper surface: Close to 144A; proximally, tinged with close to N199A. Color, lower surface: Close to 144A; proximally, tinged with close to 174B to 174C.

Inflorescence description:

*Appearance*.—Composite inflorescence form with oblanceolate-shaped ray florets; solitary inflorescences borne on upright and strong scapes above the foliar plane; ray and disc florets arranged acropetally on a capitulum.

*Fragrance*.—None detected.

*Flowering season*.—Plants begin flowering about three months after planting; under garden conditions in The Netherlands, plants flower from early spring to late summer; plants can be flowered year-round in the greenhouse.

*Inflorescence longevity*.—Depending on the temperature, inflorescences last about two weeks on the plant; inflorescences not persistent.

*Quantity of inflorescences*.—Freely flowering habit with about eleven open and developing inflorescences per plant at one time.

*Inflorescence buds*.—Height: About 1.7 cm. Diameter: About 2.4 cm. Shape: Flattened globular. Color: Close to 151C to 151D; towards the apex, close to 150B; towards the base, close to 137A to 137C.

*Inflorescence size*.—Diameter: About 8.5 cm. Depth (height): About 3.3 cm. Diameter of disc: About 2.6 cm. Receptacle height: About 3 mm. Receptacle diameter: About 5 mm. Receptacle color: Close to 157D.

*Ray florets*.—Quantity and arrangement: About 52 per inflorescence arranged in about three whorls. Orientation: About 40° from horizontal. Length: About 4.1 cm. Width: About 1.1 cm. Shape: Oblanceolate. Apex: Retuse to obtuse. Base: Cuneate. Margin: Entire. Texture, upper surface: Smooth, glabrous; velvety. Texture, lower surface: Smooth, glabrous; slightly velvety. Color: When opening, upper surface: Close to 41A. When opening, lower surface: Close to 151C; central band strongly tinged with close to 31A. Fully opened, upper surface: Close to N30A; color becoming closer to 33A with development. Fully opened, lower surface: Close to 26A and 28B; colors becoming closer to 26B and 29A with development.

*Disc florets*.—Quantity and arrangement: About 300 massed at center of receptacle. Length: About 1.4 cm. Width: About 4 mm. Shape: Tubular. Apex: Acute. Base: Lower 80%, fused. Margin: Entire. Texture, upper and lower surfaces: Smooth, glabrous. Color, prior to opening: Apex: Close to 32B. Mid-section: Close to 6D. Base: Close to 152D. Color, when opening: Apex: Close to 33B. Mid-section: Close to 6D. Base: Close to 152D. Color, fully opened: Apex: Close to 40B. Mid-section: Close to 8C. Base: Close to 20A.

*Pappus*.—Quantity of hairs per floret: About 50. Length: About 7 mm. Diameter: Less than 1 mm. Texture: Soft. Color: Close to 158D.

*Phyllaries*.—Quantity and arrangement: About 70 per inflorescence arranged in about three whorls. Length: About 1.8 cm. Width (at base): About 2 mm. Shape: Lanceolate. Apex: Narrowly acute. Base: Cuneate. Margin: Entire. Texture, upper surface: Smooth, glabrous. Texture, lower surface: Densely tomentose. Color, upper surface: Close to 143B. Color, lower surface: Close to 137B to 137C.

*Scapes*.—Length: About 26 cm. Diameter: About 7 mm; distally, about 4.5 mm. Angle: About 20° from vertical. Strength: Strong. Texture: Densely tomentose. Color: Close to 144A; distally, close to 147B.

*Reproductive organs*.—Androecium (present on disc florets only): Quantity per floret: Five. Filament length: About 8 mm. Filament color: Close to 11D. Anther shape: Lanceolate. Anther length: About 4 mm. Anther color: Close to 150B. Pollen amount: Scarce. Pollen color: Close to 13B. Gynoecium (present only on ray florets): Quantity per floret: One. Pistil length: About 8 mm. Stigma shape: Cleft. Stigma color: Close to 11A. Style length: About 7.5 mm. Style color: Close to 11B to 11C. Ovary color: Close to 145D.

*Seeds and fruits*.—Seed and fruit production has not been observed on plants of the new *Gerbera*.

Disease & pest resistance: Resistance to pathogens and pests common to *Gerbera* plants has not been observed on plants of the new *Gerbera* grown under commercial production conditions.

Garden performance: Plants of the new *Gerbera* have been observed to have good garden performance, to tolerate high temperatures about 35° C. and to be cold hardy to USDA Hardiness Zone 7.

It is claimed:

1. A new and distinct *Gerbera* plant named 'Garglow Imp' as illustrated and described.

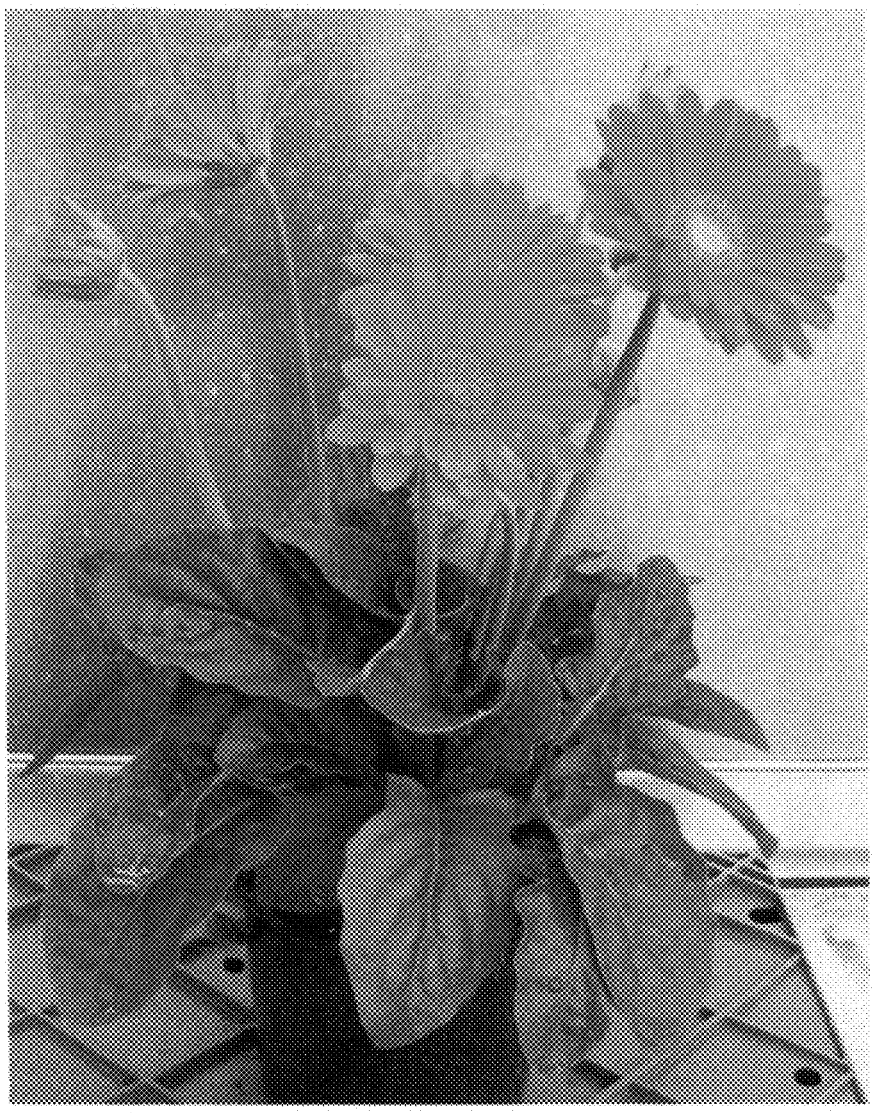

* * * * *